(12) United States Patent
Stoven et al.

(10) Patent No.: US 6,635,627 B1
(45) Date of Patent: Oct. 21, 2003

(54) ANTI-CANCER PRODUCTS FOR TREATING CYSTIC FIBROSIS

(75) Inventors: Véronique Stoven, Paris (FR); Gérard Lenoir, Paris (FR); Jean-Yves Lallemand, Palaiseau (FR); Jean-Philippe Annereau, Paris (FR); Joël Barthe, Paris (FR); Sylvain Blanquet, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/424,785

(22) PCT Filed: May 28, 1998

(86) PCT No.: PCT/FR98/01074

§ 371 (c)(1),
(2), (4) Date: Nov. 29, 1999

(87) PCT Pub. No.: WO98/53839

PCT Pub. Date: Dec. 3, 1998

(30) Foreign Application Priority Data

May 30, 1997 (FR) .............................. 97 06667

(51) Int. Cl.⁷ .............................................. A61K 31/66
(52) U.S. Cl. ............................................................ 514/110
(58) Field of Search ................................. 514/110, 851

(56) References Cited

FOREIGN PATENT DOCUMENTS

| EP | 0 715 853 | 6/1996 |
|---|---|---|
| WO | WO 94/25607 | 11/1994 |
| WO | WO 96/01627 | 1/1996 |

OTHER PUBLICATIONS

Akimaru, "Induction of MRP/GS-X Pump and Cellular Resistance to Anticancer Prostaglandins" *Cytotechnology* vol. 19, No. 3, pp. 221–227 (1996).

G. Jedlitschky et al., "Transport of Glutathione, Glucuronate, and Sulfate Conjugates by the MRP Gene–encoded Conjugate Export Pump", Cancer Research, vol. 56, pp. 988–994, (1996).

J–R Yi et al., "Expression Cloning of the cDNA for a Polypeptide Associated with Rat Hepatic Sinusoidal Reduced Glutathione Transport: Characteristics and Comparison with the Canalicular Transporter", Proc. Natl. Acad. Sci., U.S.A., vol. 92, No. 5, pp. 1495–1499, (1995).

G. Jedlitschky et al., "ATP–Dependent Transport of Glutathione S–Conjugates by the Multidrug Resistance–Associated Protein", Cancer Research, vol. 54, No. 18, pp. 4833–4836, (1994).

G. Jedlitschky et al., "ATP–Dependent Glutathione Conjugate Transport in HL60 Cells Overexpressing the Multidrug Resistance Associated Protein (MRP)", Anti–Cancer Drugs, vol. 5, Suppl. 1, p. 4, (1994).

M. Müller et al., "Overexpression of the Gene Encoding the Multidrug Resistance–Associated Protein Results in Increased ATP–Dependent Glutathione S–Conjugate Transport", Proc. Natl. Acad. Sci., U.S.A., vol. 91, pp. 13033–13037, (1994).

T. Ishikawa, et al., "How Does the MRP/GS–X Pump Export Doxorubicin?", J. Natl. Cancer Inst., vol. 87, No. 21, pp. 1639–1640, (1995).

I. Leier et al., "ATP–Dependent Glutathione Disulphide Transport Mediated by the MRP Gene–Encoded Conjugate Export Pump", Biochem. J., vol. 314, No. 2, pp. 433–437, (1996).

S. Demolombe et al., "ATP–Binding Cassette Proteins as Targets for Drug Discovery", TIPS, vol. 17, No. 8, pp. 273–275, (1996).

T. Ishikawa et al., "The GS–X Pump in Plant, Yeast, and Animal Cells: Structure, Function, and Gene Expression", Bioscience Reports, vol. 17, No. 2, pp. 189–207, (1997).

Y.H. Ko et al., "The Cystic Fibrosis Transmembrane Conductance Regulator", The Journal of Biological Chemistry, vol. 268, No. 32, pp. 24330–24338, (1993).

Y.H. Ko et al., "The First Nucleotide Binding Fold of the Cystic Fibrosis Transmembrane Conductance Regulator Can Function as an Active ATPase", The Journal of Biological Chemistry, vol. 270, No. 38, pp. 22093–22096, (1995).

J.A. Cohn et al., "Regulation of the NBD1/R Domain of CFTR by ATP and by Protein Kinases", Gastroenterology, vol. 112, No. 4 Suppl., p. A355, (1997).

R. Mayer et al., "Expression of the MRP Gene–Encoded Conjugate Export Pump in Liver and Its Selective Absence from the Canalicular Membrane in Transport–Deficient Mutant Hepatocytes", The Journal of Cell Biology, vol. 131, No. 1, pp. 137–150, (1995).

(List continued on next page.)

Primary Examiner—Theodore J. Criares
Assistant Examiner—Jennifer Kim
(74) Attorney, Agent, or Firm—Finnegan, Henderson, Farabow, Garrett & Dunner, L.L.P.

(57) ABSTRACT

The invention concerns a novel approach for treating cystic fibrosis using, in particular, anti-cancer chemotherapy. For the treatment of cystic fibrosis it proposes the use of at least one product which when administered to a patient brings about the expression or overexpression of an ABC carrier compound, in particular glutathione carrier. Preferably, the products used are anti-cancer products whose administration brings about the expression of MRP and/or MDR protein. The invention is also applicable to the treatment of rheumatoid polyarthritis or asthma. More specifically, the compounds are selected among cyclophosphamide, aclarubicin, doxorubicin, daunorubicin, epirubicin, idarubicin, zorubicin, pirabucin, colchicine, videsine, vinorelbine, vincristine, binblasine, azithromycin, erythromycin, ifosmamide, N-acetyl cysteine, N-acetyl lysine and/or a CFTR protein fragment comprising the NBF1 domain.

16 Claims, 2 Drawing Sheets

OTHER PUBLICATIONS

Figure 1:
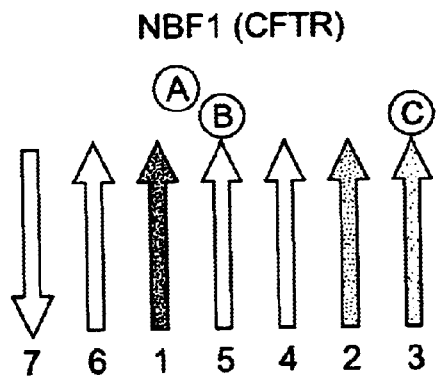

C. Guay–Broder et al., "$A_1$ Receptor Antagonist 8–Cyclopentyl–1,3–Dipropylxanthine Selectively Activates Chloride Efflux from Human Epithelial and Mouse Fibroblast Cell Lines Expressing the Cystic Fibrosis Transmembrane Regulator ΔF508 Mutation", Biochemistry, vol. 34, No. 28, pp. 9079–9087, (1995).

S.H. Cheng et al., "Functional Activation of the Cystic Fibrosis Trafficking Mutant ΔF508–CFTR by Overexpression", American Journal of Physiology, vol. 268, No. 4, Part 1, pp. L615–L624, (1995).

W. Breuer et al., "Induction of Multidrug Resistance Downregulates the Expression of CFTR in Colon Epithelial Cells", American Journal of Physiology, vol. 265 (6 Pt 1), pp. C1711–C1715, (1993).

H. Kobayashi et al., "Biofilm Disease: Its Clinical Manifestation and Therapeutic Possibilities of Macrolides", The American Journal of Medicine, vol. 99, Suppl. 6A, pp. 26S–30S, (1995).

Ph. Reinert, "Effets De L'Azithromycine Sur La Virulence Du Pyocyanique", Pathologie Biologie, Vol. 43, No. 6, pp. 551–553, (1995).

E. Puchelle, "CFTR (Cystic Fibrosis Transmembrane Conductance Regulator): Une Protéine A Multiples Fonctions", M/S Médecine Sciences, vol. 10, No. 6–7, pp. 627–629, (1994).

E. Dagli, et al., "Use of Low–Dose Methotrexate for Anti–Inflammatory Treatment of Advance Cystic Fibrosis", Am. Rev. Respir. Dis., vol. 141, No. 4, Part 2, p. A812, (1990), (Abstract Only).

A. Bauernfeind et al., "Staphylococcal Aspects of Cystic Fibrosis", Infection, vol. 18, No. 2, pp. 126–130, (1990).

J.Y. Lallemand et al., Induction by Antitumoral Drugs of Proteins that Functionally Complement CFTR: A Novel Therapy for Cystic Fibrosis?, The Lancet, vol. 350, pp. 711–712, (1997).

E. Kuwertz–Bröking et al., Colchicine for Secondary Nephropathic Amyloidosis in Cystic Fibrosis, The Lancet, vol. 345, pp. 1178–1179, (1995).

R.J. MacLeod et al., "Developmental Differences of Cystic Fibrosis Transmembrane Conductance Regulator Functional Expressions in Isolated Rate Fetal Distal Airway Epithelial Cells", Pediatric Research, vol. 35, No. 1, pp. 45–49, (1994).

J.H. Roum et al., "Systemic Deficiency of Glutathione in Cystic Fibrosis", Journal of Applied Physiology, vol. 75, No. 6, pp. 2419–2424, (1993).

Ch. Maayan et al., "Immediate Effect of Various Treatments on Lung Function in Infants with Cystic Fibrosis", Respiration, vol. 55, No. 3, pp. 144–151, (1989).

H. Fischer et al., "The Actin Filament Disrupter Cytochalasin D Activates the Recombinant Cystic Fibrosis Transmembrane Conductance Regulator $Cl^-$ Channel in Mouse 3T3 Fibroblasts", Journal of Physiology, vol. 489, Part 3, pp. 745–754, (1995).

J.P. Annereau et al., "Insight Into Cystic Fibrosis by Structural Modelling of CFTR First Nucleotide Binding Fold (NBF1)", C.R. Acad. Sci., Paris, vol. 320, No. 2, pp. 113–121, (1997).

J.P. Annereau et al., "A Novel Model for the First Nucleotide Binding Domain of the Cystic Fibrosis Transmembrane Conductance Regulator", FEBS Letters, vol. 407, No. 3, pp. 303–308, (1997).

ANTI-CANCER PRODUCTS FOR TREATING CYSTIC FIBROSIS

This Application is a 371 of PCT/FR98/01074 filed May 28, 1998, which claims priority from France 97/06667 filed May 30, 1997.

The present invention relates to a novel approach for treating cystic fibrosis which involves chemotherapy, in particular anticancer chemotherapy.

Cystic fibrosis is a genetic disease which is expressed in particular in the lungs and which is due to a defect in the gene encoding the CFTR (standing for "Cystic Fibrosis Transmembrane Conductance Regulator") protein, which is a protein which is able to participate directly or indirectly in the transport of chloride ions across the cell membranes.

In a general way, the CFTR protein belongs to the ABC (standing for "ATP Binding Cassette") transporter family, which is a very extensive family of proteins whose members are found both in eukaryotes and in prokaryotes. In general, these proteins are active transporters which hydrolyze ATP in order to supply the chemical potential which is required for their transport function. Thus, in eukaryotes, they transport various types of molecule across the cell membranes. Molecules which are capable of being transported and which may be mentioned include ions, vitamins, peptides, sugars and medicinal substances or other drugs. Their overall organization has common features: they generally comprise a transmembrane (TM) region, which is involved in selecting the chemical entity to be transported, and a nucleotide-binding domain which hydrolyzes the ATP in order to supply the chemical potential which is required for the transport (NBF standing for "Nucleotide Binding Fold").

The genes which encode these proteins are often derived from the fusion of two genes of analogous structure.

The structure of the corresponding proteins is then generally as follows:

(TM1)-(NBF1)-(TM2)-(NBF2)

The CFTR protein constitutes a 1480-amino-acid-containing member of a subfamily of the ABC transporter family termed the MRP/CFTR subfamily. In addition to the CFTR protein, this subfamily contains the human MRP protein. Specifically, the two proteins exhibit a sequence similarity of approximately 50%. The MRP (standing for "Multi-drug Resistance associated Protein") is known to be involved in phenomena of multiresistance to the medicaments which are used in cancer chemotherapy (M. Dean, R. Allikmets, Current Opinion in Genetics & Development, 5, 779–785, 1995). The CFTR protein is also structurally very close to another member of the MRP/CFTR subfamily, i.e. the protein YCF1 (standing for "Yeast Cadmium Resistance Factor 1"), which confers on the yeast Saccharomyces cerevisiae the phenotype of resistance to cadmium ions (Tommasini et al., PNAS, 93, 6743–6748, 1996). As well as their similarity in structure, the MRP and YCF1 proteins function in a similar way: they export molecules and ions in the form of their adducts with glutathione (G. J. Zaman et al., PNAS, 92, 7690–7694, 1995).

The CFTR protein also displays not insignificant structural similarities with the yeast STE6 protein, which transports the pheromone "factor a" in the yeast Saccharomyces cerevisiae (J. L. Teem et al., Cell, 73, 335–346, 1993) and with the human MDR (standing for "Multi-drug Resistance Protein") protein, which is known, like MRP, to be involved in the phenomena of multiresistance to anticancer medicaments. The human MDR protein and the STE6 protein belong to another subfamily of ABC transporters, termed the MDR/TAP subfamily.

Thus, the general adherence of the CFTR protein to the ABC transporter family, and its function of transporting chloride ions, are now well known.

In a patient suffering from cystic fibrosis, the CFTR protein is mutated. While more than 600 mutations have been recorded, the mutation involved is, in approximately 70% of cases, the deletion of a phenylalanine in position 508 in the NBF1 part ($\Delta$F508) of the overall structure of the protein. It appears that this mutation results in a defect in the folding of the protein which is then destroyed within the cell without completing its post-translational maturation (Riordan J. R., Rommens J. M., Kerem B. S., Alon N., Rozmahel R., Grzelczack Z., Zielenski J., Lok S., Plavic N., Chou J. L., Drumm M. L., Iannuzzi M. C., Collins F. S., Tsui L. C. (1989) Science. 245, 1066–1072). The absence of a mature or functional CFTR protein leads to a defect in the secretion of chloride ions. The so-called "sweat" test, which measures the secretion of chloride ions, was, moreover, developed in 1953 and remains indispensable for diagnosing cystic fibrosis.

Up to now, attempts have been made to treat cystic fibrosis by gene therapy, by means of developing systems for administering to patients a nucleic acid which encodes the wild-type CFTR protein and which is transported either by viruses or by cationic lipids. Attempts have been made to administer such a DNA/cationic lipid complex to lungs of mice by the intratracheal route (Yoshimura et al., Nucleic Acid Research, 20 :3233–3240, 1992) or by means of an aerosol (Stribling et al., Proc. Natl. Acad. Sci. 89:11,277–11,281, 1992). It has also been observed that administering the CFTR-encoding gene, in a complex together with cationic lipids, to a mouse model suffering from cystic fibrosis had the effect of correcting the defect in the function of the chloride ion channel (Hyde et al., Nature 362:250–255, 1993).

Thus, the therapeutic approaches which are currently envisaged in the case of cystic fibrosis are solely aimed at the genetic defect (mutation in the gene encoding the CFTR protein), which they are endeavoring to correct. They link the efficacy of the treatment to the re-establishment of the only chloride-ion channel function which is exerted by a functional CFTR protein.

However, even though the defect in the transport of chloride ions is indeed a clinical manifestation of cystic fibrosis, other manifestations have still not been fully explained.

Thus, as an example, the organs which are chiefly affected in cystic fibrosis are those in which glutathione is secreted, in particular the liver, or those in which detoxification mechanisms are likely to involve glutathione (lungs, intestine, colon).

Furthermore, it has been noted that the inflammatory reaction is excessive in patients suffering from cystic fibrosis. A chronic inflammation of the airways is often observed in these patients. When this occurs, a very high number of neutrophilic granulocytes is present in the airways of the patients, even when there is no detectable infection. It is possible that this inflammation precedes the appearance of the chronic infection. This influx of neutrophilic granulocytes results in a massive release of free radicals and hyperoxides in the cells of the airways of the patients. Now, it is known that exocellular and intracellular glutathione plays a central role in the control of the inflammatory reaction by protecting the cells from attack by these oxidizing agents. However, this protection appears to be impaired in patients suffering from cystic fibrosis. It would therefore appear that cystic fibrosis prevents glutathione from playing its customary role.

Studies performed on the family of ABC transporter proteins have demonstrated their relative versatility. Even though each of the proteins possesses its own function, they appear to display a shared mode of operation which enables them to undertake shared functions. For example, it has been demonstrated in vitro that the human MRP protein is able to act as a substitute for YCF1 in yeast and to undertake the function of detoxifying cadmium in this organism (Tomassini et al., PNAS, 93, 6743–6748, 1996). It can also act as a substitute for the STE6 protein in yeast in order to undertake the transport of factor a in this organism (J. L. Teem et al., Cell, 73, 335–346, 1993). Similarly, an STE6 chimeric protein, in which the CFTR NBF1 domain has been substituted for the STE6 NBF1 domain, is functional and efficiently transports factor a (J. L. Teem et al., Cell, 73, 335–346, 1993). Finally, it would appear that, in vivo, the genes which encode the CFTR, MDR and MRP proteins are under coupled transcriptional controls (Trezise A. E., Romano P. R., Gill D. R., Hyde S. C., Sepulveda F. V., Buchwald M., Higgins C. F., EMBO J., 11, 4291–4303, 1992 & M. A. Izquierdo, J. J. Neezfjes, A. E. L. Mathari, M. J. Flens, G. L. Scheffer, R. J. Scheper, British Journal of Cancer, 74, 1961–1967, 1996).

The inventors have now found that it is possible, surprisingly, to use this versatility in the ABC transporter proteins to conceive of treating cystic fibrosis by chemotherapy, by administering certain types of product to the patient. Said administration would lead to the expression or overexpression of a compound which is able to play the role of a functional CFTR protein and therefore overcome the deficiencies in the mutated CFTR protein.

For this reason, the invention relates to the use, for preparing a medicament which is intended for preventing and/or treating cystic fibrosis, of at least one product whose administration to a patient suffering from cystic fibrosis leads, in said patient, to the expression or overexpression of at least one ABC transporter compound.

It is assumed that, in the case of treating cystic fibrosis, the mechanism of action of the compound which is expressed or overexpressed is such that the compound is able to act as a substitute for the CFTR protein which is defective in the patient. It is assumed that the compound then exerts a function which is normally fulfilled by the wild-type CFTR protein and which the defective CFTR protein is unable to fulfill in the patient suffering from cystic fibrosis.

Thus, products which can be used for treating cystic fibrosis are those which are able to induce, in the body of the patient, the expression or overexpression of an ABC transporter compound, which acts as a substitute for the defective CFTR protein.

Different embodiments are conceivable. According to a first embodiment, it is possible to conceive of administering products which induce the expression or overexpression of the patient's mutated CFTR protein. This protein would then be expressed at a level which was such that it recovered its ability to function despite the presence of a mutation.

According to another embodiment, products will be selected which lead to the expression or overexpression of the MDR protein.

Furthermore, studies carried out by the inventors suggest that, in addition to its role as a chloride ion channel, the CFTR protein plays the role of a glutathione pump. This hypothesis could account for a number of clinical manifestations which are exhibited by patients who are suffering from cystic fibrosis and in whom the CFTR protein is nonfunctional.

In addition, the inventors have demonstrated the existence of a potential glutathione-binding site in the NBF1 domain of the CFTR protein, a fact which could account for the role played by glutathione in the transporter function exercised by the CFTR protein. If the CFTR protein did have a role as a glutathione pump, this could, in particular, make it possible to obtain a better understanding of the chronic inflammation which is characteristic of cystic fibrosis. This is because glutathione is a key molecule in the triggering and control of the inflammatory reaction. While it is involved in the metabolism of pro-inflammatory compounds such as the leukotrienes, it is also involved, as an agent which protects against the oxidizing agents which are released by the neutrophilic granulocytes (free radicals, hydroperoxides, etc.), in controlling these reactions.

For this reason, the invention relates, more specifically, to the use, for preparing a medicament which is intended for preventing and/or treating cystic fibrosis, of at least one product whose administration to a patient suffering from cystic fibrosis leads, in said patient, to the expression or overexpression of an ABC compound which is a glutathione transporter.

According to the invention, "compound which is a glutathione transporter" is understood as being a compound which belongs to the already itemized family of ABC transporters which exercise their transport function through the agency of glutathione. It is also understood as meaning any fragment or analog of such a transporter which results from one more mutations and which retains the property of transporting through the agency of glutathione.

Glutathione is understood as being glutathione itself or its adducts with other compounds. These adducts can be natural adducts, such as the leukotrienes, or detoxification adducts with heavy metals, powerful oxidizing agents (free radicals, peroxides, etc.) or drugs.

This is because it has already been established that some proteins, in particular the human MRP protein, export drugs and medicaments, in particular anticancer products, through the agency of glutathione, either in the form of direct glutathione-drug adducts or by simultaneously or sequentially binding glutathione and the drug (G. J. Zaman et al., PNAS, 92, 7690–7694, 1995).

According to a particularly preferred embodiment, an attempt will be made to express or overexpress the MRP protein. In this case, but also in the more general case where the expressed or overexpressed compound is an ABC transporter, in particular the MDR protein, the products which can be used in accordance with the invention are preferably anticancer products of the antineoplastic type, that is to say cytotoxic anticancer agents which, for treating cancer, have to kill the target cancer cells as selectively as possible. In fact, it is known that administering these anticancer agents to patients suffering from cancer often has a tendency to give rise to phenomena of resistance to anticancer agents of the pharmacokinetic type, which phenomena are caused by the overexpression of proteins of the MRP or MDR type (M. Dean, R. Allikmets, Current Opinion in Genetics & Development, 5, 779–785, 1995; Jedlitschky et al., Cancer Research, vol. 56, Mar. 1, 1996, 988–994; Akimaru, Cytotechnology, vol. 19, No. 3, 196, 221–227; Jedlitschky, Cancer Research vol. 54 No. 18, 1994, 4833–4836; Jedlitschky et al., Anticancer drugs, vol. 5 suppl. 01, Sep. 4, 1994; Mueller et al., PNAS, vol. 91, 1994, 13033–13037; Ishikawa, J. Natl, Cancer Inst., vol 87, No. 21, 1995, 1639–1640; Leier et al. Biochemical Journal, vol. 314, No. 2, 1996, 433–437).

The invention is therefore directed towards using four large families of antineoplastic agents which are employed in the treatment of cancer, i.e. alkylating agents, intercalating agents, anti-metabolites and spindle poisons, for treating cystic fibrosis.

Alkylating agents are agents which are able to replace a proton, in a molecule, with an alkyl group. They significantly alter the structure of the DNA at the time of mitoses, whose progress they disrupt. Of the large families of alkylating agents which can be used in accordance with the invention, those which may be mentioned are nitrogen mustards, nitrosoureas, platinum derivatives, ethyleneimine derivatives, dimethane sulfonoxyalkanes, piperazine derivatives and methylhydrazine derivatives. Representative examples of nitrogen mustards are chlorambucil, cyclophosphamide, ifosfamide, estramustine, melphalan and chlormethine. Use is advantageously made of ifosfamide, in particular in combination with an intercalating agent.

The intercalating agents are agents which intercalate between the two complementary strands of the DNA, thereby blocking replication of the DNA, transcription into mRNA and protein synthesis. The large families which can be used in accordance with the invention comprise, in a nonlimiting manner, anthracyclines, anthraceredziones, anthracenes, acridine derivatives, ellipticines and actinomycins. Preference is given to using anthracyclines, among which may be mentioned, in a nonlimiting manner, aclarubicin, doxorubicin, daunorubicin, epirubicin, idarubicin, zorubicin and pirabucin. Preference is given to using epirubicin, in particular in combination with ifosfamide.

A third family of compounds which can be used in accordance with the invention is represented by antimetabolites, or antagonists, or structural analogs which generally inhibit one or more steps in nucleic acid synthesis. These compounds are represented, in a nonlimiting manner, by folic acid antagonists, purine antagonists and pyrimidine antagonists. Particular mention may be made of amethopterin (methotrexate), mercaptopurine, 5-fluorouracil and cytarabine.

Another category of anticancer agents is represented by the spindle poisons, which block cell mitosis. These are anti-mitotic agents whose representative families are the epipodophyllotoxins and the vinca alkaloids. Epipodophyllotoxins which may be mentioned are teniposide and etoposide. Examples of vinca derivatives which may be mentioned are vindesine, vinorelbine, vincristine and vinblastine. Preference will be given to mentioning colchicine and its derivatives. Particularly satisfactory results have been obtained with colchicine, which is all the more advantageous since this product is known to be of low toxicity.

Finally, mention must also be made of the taxoid family (taxol, taxotere, etc.).

According to another embodiment, it is also possible to use various cytolytic agents such as, for example, bleomycin, dacarbazine, hydroxycarbamide, asparaginase, mitoguazone and plicamycin.

Mention will more particularly be made of sodium phenylbutyrate, which is a cytostatic agent which is used in diseases of the urea cycle accompanied by hepatic manifestations.

Mention will also be made, as products which can be used in accordance with the invention, of the products of the macrolide family which are known for their properties of inducing overexpression of the MDR protein, leading to the phenomenon of drug resistance (MDR). Examples of these inducers are those mentioned in the publication Seelig Eur. J. Biochem., 25, 252–261 (1998).

A number of these have already been mentioned as belonging to the anticancer agents. These inducers comprise, in particular, actinomycin D, clotrimazole, colchicine, daunorubicin, doxorubicin, epothilone A, erythromycin, eroposide, isosafrole, midazolam, nifedipine, phenobarbital, puromycin, reserpine, rifampicin, taxol, vinblastine, vincristine, cysteine methyl ester, epinephrine and farnosol.

By way of example, mention may preferably be made of azithromycin, which is administered at doses lower than those required for obtaining an antibacterial activity (Jaffe et al., Lancet 1998; 351–420).

Another example of an MDR-protein-inducing macrolide which can be used in accordance with the invention is erythromycin (Grant et al., Toxicol. Appl. Pharmacol., 1995; 133:269–76).

In a more general manner, the studies carried out by the inventors make it possible to select products which are capable of being used in the prevention and/or treatment of cystic fibrosis by properly proportioning the mRNAs of the CFTR, MRP and MDR proteins in the cells of the patients. According to a preferred embodiment, the products which can be used are therefore those whose administration leads to the appearance of, or to an increase in, the mRNAs which correspond to these proteins and therefore, in particular, to expression or overexpression of the MRP and/or MDR protein and/or, where appropriate, the CFTR protein itself.

It can also be particularly worthwhile to test, for example, products which are not sufficiently toxic toward cells to be active in anticancer therapy but which are nevertheless sufficiently active to give rise to a "multidrug resistance" (MDR) phenomenon which can be taken advantage of within the context of the present invention.

All these compounds can be used under conditions which suffice to activate expression or overexpression of the MRP protein and/or the MDR protein and/or the CFTR protein.

Polychemotherapy by general, intermittent and sequential means is commonly used for the therapy of cancer. It is also possible to envisage using this type of treatment in accordance with the invention.

The invention therefore also relates to the use, for preparing a medicament which is intended for preventing and/or treating cystic fibrosis, of a product which contains at least one anticancer agent and/or macrolide as a combination product for simultaneous or separate use or for use which is staggered over time.

Preferably, said combination product will comprise an alkylating agent and an intercalating agent, and, even more preferably, the alkylating agent is ifosfamide and the intercalating agent is epirubicin.

The products which can be used in accordance with the invention are preferably administered together with a glutathione precursor, for simultaneous or separate use or for use which is staggered over time. In fact, it has often been observed that patients suffering from cystic fibrosis are deficient in glutathione and that administration of a glutathione precursor promotes an increase in the glutathione level. When the administered products are anticancer products which induce expression or overexpression of the MRP protein, the joint administration of a glutathione precursor is particularly desirable since the activity of the MRP protein depends on glutathione. Examples of glutathione precursors which may be mentioned are N-acetylcysteine (for example that marketed under the name Mucomyst) and N-acetyllysine.

The present invention also includes a second aspect. According to this aspect, a compound which directly replaces the defective CFTR protein, by playing the role of glutathione transporter, is administered to the patient.

The invention therefore also relates to a glutathione transporter compound as a medicament for secondarily preventing, and/or treating, cystic fibrosis. Some authors have already cloned a glutathione transporter compound into a rat liver (Yi et al., PNAS vol. 92, No. 5, 1995, 1495–1499). However, the possibility of a link with cystic fibrosis has never been considered.

Figure 3:
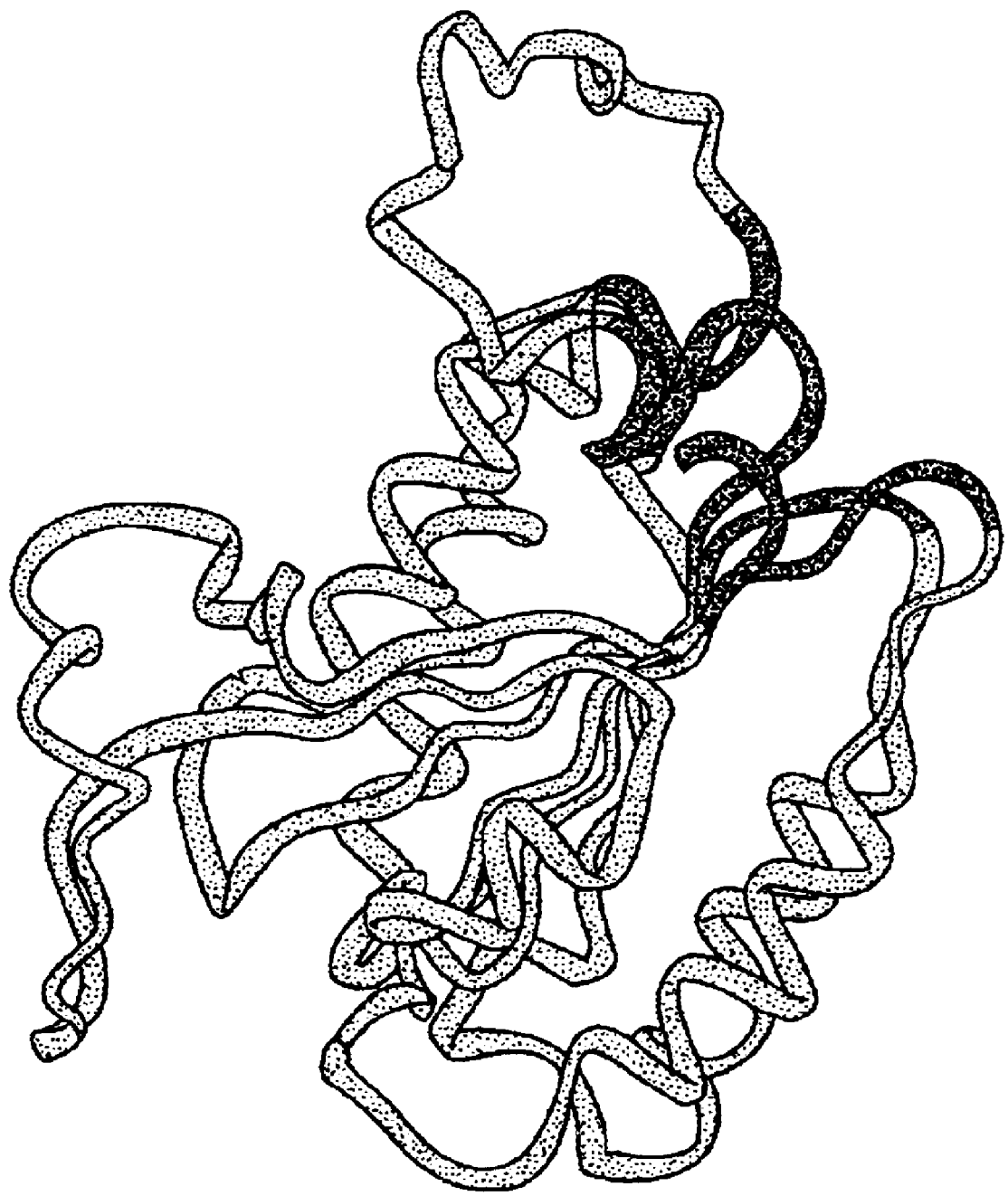

Preferably this compound will be a fragment of a glutathione transporter ABC compound, in particular a fragment of the CFTR protein which comprises the NBF1 domain and, more specifically, a fragment which comprises the potential glutathione-binding site which is identified by reference to FIG. 3 in the examples which follow. The fragment is preferably a fragment which contains the residues I448-Q452, S478-K481, M498-I506, A566-L568, A596-T599, which are located in loops which are situated at the N-terminal ends of β-pleated sheets 1 to 3 of the NBF1 domain. The joint administration of a glutathione precursor is also advantageous.

Finally, the invention relates to the application of the treatment according to the invention for treating rheumatoid arthritis or particular forms of asthma as well. These inflammatory pathologies are also likely to be initially caused by a defect in glutathione transport. Furthermore, they occur frequently in patients suffering from cystic fibrosis or in cystic fibrosis heterozygotes which only carry one modified allele out of the two for the CFTR gene.

Figure 2:
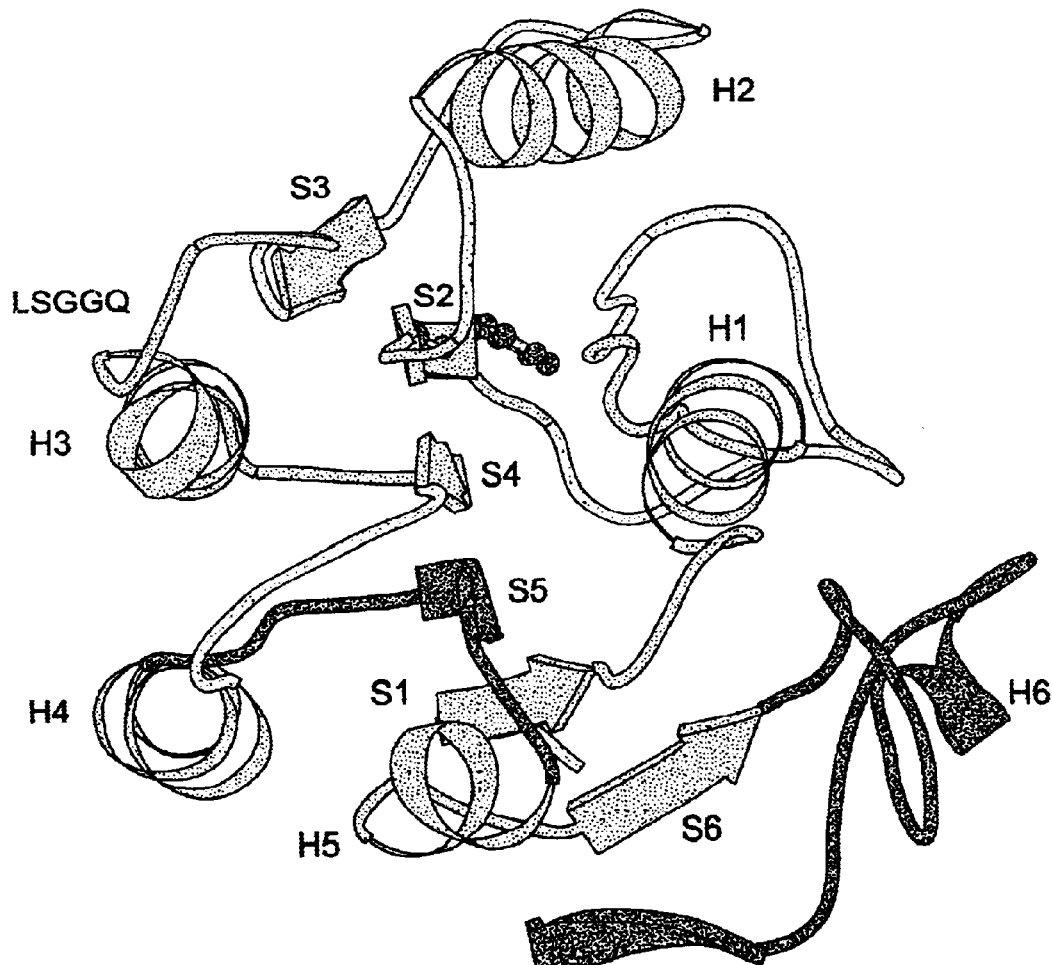

Other features and advantages of the invention will appear during the following detailed description of examples of implementing the invention, which description is illustrated by FIGS. 1 to 3, which depict the structure of the NFB1 domain of the CFTR protein and the location of the potential glutathione-binding site in the CFTR protein.

FIG. 1 depicts the topology of the central β-pleated sheet of a model of NBF1. It comprises a β-pleated sheet having six parallel strands whose pairing is given. A seventh strand is paired in an antiparallel manner (strands 1 to 6 are, respectively: L453-G458, N505-S511, N538-G542, D567-D572 and R600-V603. Strand 7 comprises the residues K643-D648). The positions of the Walker A and B consensus sequences and the ABC signature are indicated.

FIG. 2 is a diagrammatic model of the NBF1 domain of the CFTR protein. β-pleated sheets 1 to 7 are marked S1 to S7. The helices 1 to 6 are shown as H1 to H6. The position of the ABC signature (sequence LSGGQ) is shown. The position of phenylalanine 508 is shown by a CPK representation on strand S2.

FIG. 3 depicts a model of the NBF1 domain of the CFTR protein in which the residues which are potentially involved in binding glutathione are depicted in dark gray.

EXAMPLE 1

Studying the Structure of the CFTR Protein
Experimental Method
1. Constructing the Plasmid The gene encoding the NBF1 domain of the CFTR protein (sequence R450-I586) is introduced into *E. coli*. For this, the complete CFTR cDNA was supplied by Transgene (Strasbourg, France). The DNA fragment encoding NBF1 was amplified by PCR. The oligonucleotides 5'-GC AGA TCT AGA GGA CAG TTG TT-3' (SEQ ID NO. 1) and 3'-TA CAA AAT TGT CTT TTT CTT ATT CTT AAG CG-5' (SEQ ID NO. 2) were used for the preamplification. The amplification product was introduced, using the Bam HI and Eco RI restriction sites, into the plasmid pGEX-KT (Hakes and Dixon, Anal. Biochem., 202, 293–298, 1992). In this plasmid, NBF1 is produced in the form of a fusion protein together with Glutathione-S-Transferase (GST). A flexible polyglycine linker sequence and a site for cutting with thrombin separate the GST and the NBF1 in the fusion protein. The gene encoding this fusion protein was sequenced and corresponds well with the expected gene. The final plasmid for this construction was introduced into a RecA-E. coli JM101TR strain.

2. Expression and Purification of the GST-NBF1 Fusion Protein

The transformed bacteria were cultured at 28° C. in an LB culture medium (15 g of Tryptone, 5 g of yeast extract, 8 g of NaCl, 0.52 g of Tris base, 100 mg of ampicillin per liter, pH 7.25). Expression of the fusion protein was induced with 0.1 mM IPTG as the OD at 600 nm (absorption frequency of the bacteria) increased from 0.8 to 2.5. The bacteria were centrifuged at 4000 g for 25 minutes and then rinsed twice with cold PBS before being sonicated. Resolubilization was achieved using a solution of PBS/0.1 mM [lacuna] and PMSF/1% Triton X100. The bacteria were sonicated in an ice bath for 5 minutes at 40 W using a small probe.

The suspension was centrifuged at 17,000 rpm for 40 minutes, and at 4° C., on a JA20 rotor (Beckman). The supernatant was incubated with 5 ml of a glutathione support (G4B Pharmacia) at ambient temperature for 30 minutes. The column was filled. The fusion protein was eluted with a 10 mM glutathione, 50 mM Tris, pH 8, solution at a flow rate of 0.05 ml/min. The fractions absorbing at 280 nm were collected and applied in portions of 500 µl to an ion exchange column (MonoQ, Pharmacia). The column was eluted with a 150 mM solution of NaCl and a 42 kD protein was identified on an SDS-PAGE gel and then confirmed by mass spectroscopy. The production yields of soluble fusion protein are 5 mg/l of culture.

3. Cutting the GST-NBF1 Fusion Protein:

Following purification, the fusion protein sample was dialyzed against a buffer (150 mM NaCl, 2.5 mM $CaCl_2$, 50 mM Tris/HC1) at pH=8. Human thrombin (T7009, Sigma) was added to give a final concentration of 5u per mg of fusion protein. The mixture was incubated at ambient temperature for 30 minutes. The products of the cutting reaction were characterized on an SDS-PAGE gel and a protein having a molecular weight of 18 kD (corresponding to the expected molecular weight of NBF1) was observed.

Results:

The GST-NBF1 fusion protein is efficiently recognized by an anti-NBF1 antibody (MATG 1061, distributed by Transgene). The affinity of this recombinant protein for ATP was verified. This involved demonstrating recognition of a fluorescent derivative of ATP (TNP-ATP). The recombinant protein was therefore produced in a functional form. However, after cutting the thrombin, it is not possible to use a similar experimental approach to that described above to separate the GST and the NBF1 domain on an affinity column which is grafted with glutathione (GSH). Although they are perfectly well separated on an electrophoresis gel, the NBF1 and GST proteins coelute on a column of immobilized GSH. This observation implies that (as anticipated for GST) NBF1 is retained on the GSH column, which is in agreement with the existence of a glutathione-binding site in NBF1.

EXAMPLE 2

Demonstration of the Presence of a Potential Glutathione-binding Site in the NBF1 Domain A structural model for the CFTR NBF1 domain (Annereau et al., C. R. Acad. Sci. Paris, Sciences de la Vie/Life Sciences, 320, 113–121, 1997 and Annereau et al., FEBS Letters, 407, 303–308, 1997) was constructed by homology with the known structure of the nucleotide-binding domains of bovine F1 ATPase (Abrahams J. P., Leslie A. G. W., Lutter R., Walker J. F., 1994 Nature, 370, 621–628). This domain comprises a hydrophobic core consisting of a β-pleated sheet having 6 parallel strands whose pairing in relation to the order in the primary sequence is given in FIG. 1 (strands 1 to 6 are respectively: L453-G458, N505-S511, N538-G542, D567-D572, R600-V603). These β-pleated sheets alternate with 6 α helices (K464-E474, Y517-D529, Q552-Y563, L581-V591, S605-K611, S631-L636). The α helices are organized on either side of the mid plane of the central β-pleated sheet, as is shown in FIG. 2 (FEBS Letters, vol. 407, pp 303–308, 1997). Loops located on the surface of the domain link the helices to the β-pleated sheets.

The potential existence of a glutathione-binding site in CFTR NBF1 which is virtually superimposable on the glutathione-binding site in GST is demonstrated by comparing this model with the known structure of GST (Glutathione-S-Transferase, a protein which possesses a glutathione-binding site and which catalyzes the nucleophilic attack reactions of the glutathione). FIG. 3 shows the NBF1 residues which are potentially involved in binding the glutathione. They are located in a region which forms a crevice at the ends of strands involved in a β-pleated sheet. More precisely, these residues are located in loops at the N-terminal ends of β-pleated sheets 1 to 4 of the NBF1 structure. These loops contain the residues I448-Q452, S478-K481, M498-I506, A566-L568, A596-T599.

EXAMPLE 3

Treating Cystic Fibrosis with a Combination of Epiribicin and Cyclophosphamide

The following antitumor treatment was administered:
epirubicin (Farmorubicine®), 110 mg for two days (D1 and D2);
ifosfamide (Holoxan®), 3.3 g for five days (D1 to D5)
Filgrastim (Neupogen®), 300 μg per day for eight days (D8 to D15); under cover of:
granisetron (Kytril®), for preventing nausea;
Methylprednisolone (Solumedrol®, corticoid);
Mesna (Mucofluid®);
the patient was then given a further six cycles of epirubicin and ifosfamide three months later.

The treated patient had a ΔF 508 genotype, which is a mutation corresponding to a deletion of a phenylalanine in position 508, in CFTR exon 12 in one allele, and another mutation, i.e. G673X, located in exon 13 in the other allele. Since his birth in 1968, this patient had exhibited all the clinical signs associated with the disease: positive sweat tests, repeated sinusites, repeated bronchites, polyps in the nasal cavity, etc. In 1989, he presented with a Pseudomonas aeruginosa infection, which is classical in cystic fibrosis and usually virtually conclusive in these patients. In addition, a fibrosarcoma of the left thigh was diagnosed in April 1993. The patient underwent a surgical and radiotherapeutic treatment and then chemotherapy from July to October 1993, followed by a new treatment in January 1994. The following improvements were observed in the clinical picture of cystic fibrosis following the chemotherapeutic treatment:

the respiratory status of the patient improved considerably;

his infection with Pseudomonas aeruginosa disappeared;

his respiratory parameters achieved approximately 75% of the theoretical values;

he recovered a respiratory status which was about equivalent to that which he had exhibited at the beginning of his adolescence;

he declared himself cured of cystic fibrosis.

A sweat test which was carried out on the patient at the beginning of 1997 turned out to be still very positive, signifying that the chloride ion channel function had not been re-established in this patient. This observation, linked to the fact that the patient declared himself cured of cystic fibrosis, suggests that another essential function was re-established by the chemotherapeutic treatment. As a result of the studies carried out by the inventors, it is now possible to assume that the function is a transport function using glutathione.

EXAMPLE 4

Demonstrating Overexpression of the MDR and MRP Proteins in the Patient Following Chemotherapeutic Treatment in Accordance with Example 3

The mRNAs of the CFTR, MDR and MRP proteins were assayed by RT-PCR, which was carried out on epithelial cells collected from the patient of Example 3 (patient A) and then analyzed. The same assay was carried out on a patient who was suffering from cystic fibrosis and who had never been exposed to anticancer products (patient B).

While the mRNAs of CFTR, MDR and MRP were not detectable in patient B, they were identified unambiguously in patient A.

These results reinforce the hypothesis which forms the basis of the invention and according to which the improvement in the clinical status of the patient will be due to CFTR being replaced with MDR and/or MRP. This is because, even when overexpressed, the mutated CFTR protein is, a priori, nonfunctional.

EXAMPLE 5

Treating Cystic Fibrosis with Chemotherapy Which is Prescribed for a Lymphoma.

The patient, who was born in 1969, suffers from cystic fibrosis, which was diagnosed at the age of two months by means of a positive sweat test. His clinical picture is typical for cystic fibrosis (exocrine pancreatic insufficiency, polyposis of the sinuses, chronic pyocyanic colonization). He is following a standard basic treatment for his cystic fibrosis: respiratory kinesitherapy, several courses of treatment with antibiotics and vitamins. In August 1992, he presents with a stage IV lymphoma. He undergoes four courses of treatment combining adriamycin, cyclophosphamide (Endoxan Asta®), cytorabine (Aracytine®), vincristine (Oncovin®), methylpred-nisolone (Depa-medrol®), Bleomycin and Methotrexate in October 1992 and November 1992. In January 1993, he undergoes a new treatment combining methotrexate, cytarabine and methylprednisolone. All chemotherapeutic treatment is stopped in April 1993. The patient is judged to have been transformed at the pulmonary level from March 1993 to December 1993, both by himself and by the doctors who are monitoring him; no more coughing, no more respiratory kinesitherapy; he exerts himself physically without difficulty and he has several normal pulmonary examinations. In the absence of maintenance chemotherapeutic treatment, some symptoms resumed from the end of 1994, such as an increase in the coughing. However, a marked improvement in the condition of the patient was noted over a period of one year following the aggressive treatment for the lymphoma.

The treated patient was homozygous for a mutation in exon 20 in the NBF2 domain.

What is claimed is:

1. A method of using a medicament for preventing and/or treating cystic fibrosis, said method comprising administering to a patient in need thereof said medicament in an amount sufficient to cause the expression or overexpression of at least one ABC transporter compound, wherein the medicament is an alkylating agent.

2. The method according to claim 1, wherein said administration leads, in said patient, to the expression or overexpression of the patient's mutated CFTR protein.

3. The method according to claim 1, wherein said expressed or overexpressed ABC transporter compound is the MDR protein.

4. The method according to claim 1, wherein said expressed or overexpressed ABC transporter compound is an ABC glutathione transporter compound.

5. The method according to claim 4, wherein said expressed or overexpressed ABC transporter compound is the MRP protein.

6. The method according to claim 1, wherein said expressed or overexpressed ABC transporter compound is the MRP protein and/or the MDR protein and/or the CFTR protein.

7. The method according to claim 1, wherein the alkylating agent is selected from nitrogen mustards, nitrosoureas, platinum derivatives, ethyleneimine derivatives, dimethane sulfonoxyalkanes, piperazine derivatives, and methylhydrazine derivatives.

8. The method according to claim 7, wherein the alkylating agent is a nitrogen mustard.

9. The method according to claim 1, wherein said medicament further comprises at least one macrolide, as a combination product, for simultaneous or separate use, or use which is staggered over time.

10. The method according to claim 9, wherein said combination product contains an alkylating agent and an intercalating agent.

11. The method according to claim 10, wherein the alkylating agent is ifosfamide and the intercalating agent is epirubicin.

12. The method according to claim 1, wherein said method further comprises administering a glutathione precursor.

13. The method according to claim 12, wherein said glutathione precursor is N-acetylcysteine or N-acetyllysine.

14. The method of claim 10, wherein said nitrogen mustard is cyclophosphamide.

15. The method of claim 12, wherein said glutathione precursor is administered simultaneously with said medicament.

16. The method of claim 12, wherein said glutathione precursor is administered as part of a product that comprises said medicament.

* * * * *

UNITED STATES PATENT AND TRADEMARK OFFICE
CERTIFICATE OF CORRECTION

PATENT NO. : 6,635,627 B1
DATED : October 21, 2003
INVENTOR(S) : Stoven et al.

It is certified that error appears in the above-identified patent and that said Letters Patent is hereby corrected as shown below:

<u>Title page,</u>
Item [57], ABSTRACT,
Line 14, "binblasine," should read -- binblastine, --

<u>Column 12,</u>
Line 46, "claims 10," should read -- claim 8, --.

Signed and Sealed this

Twentieth Day of January, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<221> NAME/KEY: misc_feature
<223> OTHER INFORMATION: 5'-3' OLIGONUCLEOTIDE

<400> SEQUENCE: 1
gcagatctag aggacagttg tt                                            22

<210> SEQ ID NO 2
<211> LENGTH: 31
<212> TYPE: DNA
<213> ORGANISM: Artificial Sequence
<220> FEATURE:
<221> NAME/KEY: misc_feature
<223> OTHER INFORMATION: 3'-5' OLIGONUCLEOTIDE

<400> SEQUENCE: 2
tacaaaattg tcttttctt attcttaagc g                                   31